United States Patent [19]

Delong

[11] Patent Number: 4,584,997

[45] Date of Patent: Apr. 29, 1986

[54] VOLUMETRIC FLOW GAUGE

[76] Inventor: Harold D. Delong, 1751-258 W. Citracado Pkwy., Escondido, Calif. 92025

[21] Appl. No.: 583,724

[22] Filed: Feb. 27, 1984

[51] Int. Cl.$^4$ ............................................. A61M 16/00
[52] U.S. Cl. ........................... 128/205.23; 128/207.18; 73/861.55; 73/198
[58] Field of Search ...................... 128/207.18, 205.23, 128/207.14; 73/198, 861.55

[56] References Cited

U.S. PATENT DOCUMENTS

| | | | |
|---|---|---|---|
| 2,099,842 | 11/1937 | Connell | 73/198 |
| 3,183,713 | 5/1965 | Gilmont | 73/861.55 |
| 3,961,624 | 6/1976 | Weigh | 128/205.23 |
| 4,158,360 | 6/1979 | Adams | 73/861.55 |
| 4,484,578 | 11/1984 | Durkan | 128/205.23 |

FOREIGN PATENT DOCUMENTS 1124404 10/1956 France ............................. 128/207.18

Primary Examiner—Henry J. Recla
Attorney, Agent, or Firm—Ralph S. Branscomb

[57] ABSTRACT

A volumetric flow gauge is provided for use particularly with ambulatory oxygen users who receive oxygen on a continuous or semi-continuous basis from an oxygen tank communicating to the patient through a line terminating in a two-tip nasal cannula, the two tips of which projects into the nostrils. The gauge comprises an upright indicator portion, having a hollow tube with a floating ball inside elevationally responsive to the upwardly directed volumetric flow of gas inside, and an integral plug spaced from the gas fitting from the indicator which plugs the second cannula tip, while the first tip receives and gauges the flow of oxygen therethrough.

10 Claims, 5 Drawing Figures

VOLUMETRIC FLOW GAUGE

BACKGROUND OF THE INVENTION

The invention is in the field of equipment and supplies for bottled oxygen users, and in particular pertains to apparatus for use to assist out-patient who use oxygen on a semi-regular, or regular basis.

There are many people suffering from emphysema and other pulmonary and cardiovascular diseases who must supplement the earth's oxygen with a supply of concentrated, bottled oxygen. This supply is ordinarily delivered to the patient through a narrow, flexible plastic tube which forks near the end to provide two tubes, encircling the head or neck from both directions to meet at a central cannula comprising a pair of parallel, short spaced tubes which are inserted into the nostrils of the patient. The patients breathes in and out normally and thus receives an extra dose of oxygen with every breath.

The amount of oxygen the patient should have supplemental to the earth's oxygen is ordinarily prescribed by the physician, and is prescribed in terms of the number of liters per minute of oxygen flow that the patient requires. Thus, a patient typically might require one liter per minute, two liters per minute, or even three or four.

The oxygen tank which the patient uses has a volumetric flow regulator which ensures that irrespective of the pressure required to deliver, the volumetric flow will be maintained at the pre-set level. Typically, the oxygen supply line passes through a humidifier bottle, which essentially bubbles oxygen up through water in a cannister. The cannister is provided with an escape valve in case the line is kinked or snarled downstream from the cannister so that the cannister will not explode as the volumetric flow regulator on the bottle continues to force oxygen into the bottle at the rate of the prescribed number of liters per minute despite the fact that the blockage has occured.

For this reason, kinks and obstructions in the line downstream of the humidifier will result in the dissipation of the prescribed oxygen to the atmosphere, without delivering it to the patient. Because some patients may have lines that are fifty feet or more long for convenience in moving about a house or apartment, it is not uncommon for the lines to get kinked. Because of the escape valve in the humidifier, the kinking may not become apparent, and many perhaps even the majority, of the oxygen users cannot feel whether or not the oxygen is being delivered through the nasal cannula. Therefore, very often the patient may not be getting the oxygen that the doctor has prescribed, or the amount that the patient thinks he is getting by the reading on the oxygen bottle.

A similar result occurs when the humidifier cannister is refilled, but the bowl is not screwed tightly enough into its gasket to prevent the escape of oxygen at pressures well below the escape valve pressure of the cannister. And, there are other ways in which the oxygen will register a certain flow rate in liters per minute at the oxygen bottle and yet not be delivered, or not be delivered in full, to the cannula. When the patient is unaware of this and cannot correct the situation, obviously the problem for which the oxygen was prescribed as a remedy will not be resolved, and the patient may suffer organ damage, unconsciousness, and in an extreme case even death.

It is not practical to measure the volumetric flow at a junction between lengths of tubing, because the connectors are so tight that even a strong, heathly person sometimes has trouble separating the tubes at a junction. There is a need, therefore, for a volumetric flow meter that can be used right at the cannula, right at the point of delivery of the oxygen to the patient so that there is no possibility of any intervening blockages between the flow meter and the oxygen.

SUMMARY OF THE INVENTION

The instant invention fulfills the above-stated need by providing a volumetric flow gauge created specifically for use at the cannula. The gauge itself has a hollow air column inside, which preferably tapers slightly toward the bottom, and which houses a ball which floats in the updraft of oxygen passing through the column from a fitting in the bottom of the tube which inserts into one tip of the cannula. An integrally molded plug fits into the other tip of the cannula to block same, so that all the oxygen which flows into and out of the cannula is forced through the fitting, and up through the slightly tapered chamber in the tube, which defines an escape hole at the top.

Thus, the patient can very easily remove the cannula from his or her nose for a few seconds, insert the gauge such that the plug and fitting seat in the respective tips of the cannula, get a quick reading along the graduated markings on the side of the transparent tube defining the tapered internal chamber and then remove the gauge and re-insert the cannula into the nostrils. The entire process can take place literally in three or four seconds, negligibly interferring with the oxygen supply to the patient.

DETAILED DESCRIPTION OF THE PREFERRED EMBODIMENT

The dotted line 1 illustrates the nose of a patient, in which the short, parallel, tubular tips 2 of the cannula 3 insert. The tubes are fairly loose, and are held in place by means not part of this disclosure. The cannula is a fairly standard way of supplying oxygen to the patient.

Figure 1:
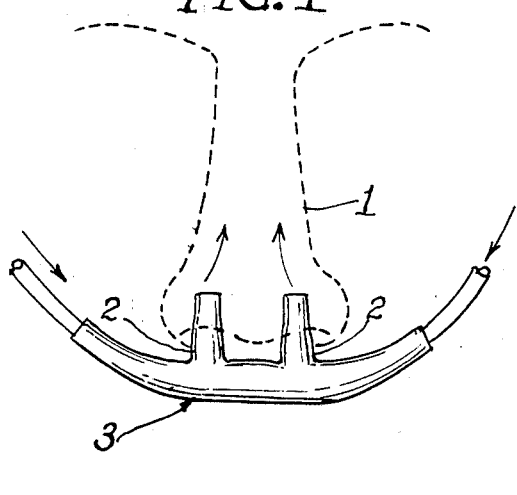
FIG. 1 is a diagrammatic view illustrating a cannula in the nostrils of a patient.
Figure 3:
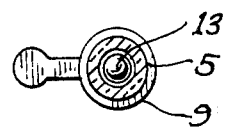
FIG. 3 is a section line 3—3 of FIG. 2.
Figure 4:
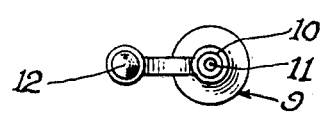
FIG. 4 is a plan view along line 4—4 of FIG. 2.
Figure 2:
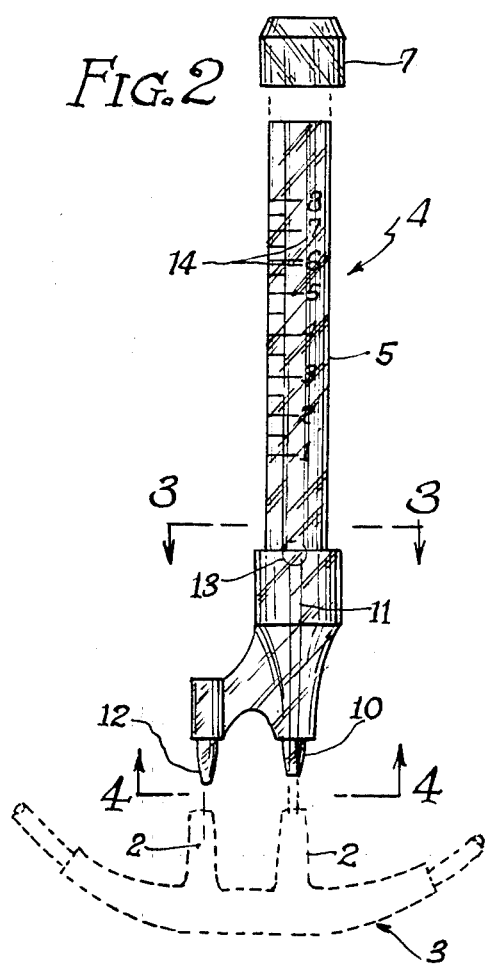
FIG. 2 is an exploded elevation view, illustrating a gauge as it fits into the tips of the cannula and with its vintage cap removed.
Figure 5:
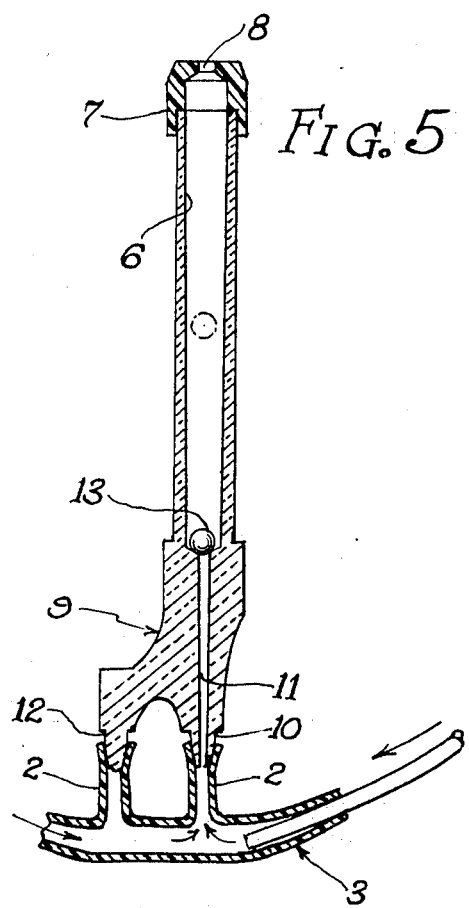
FIG. 5 is a section through the device as it seats in a cannula, taken along the plane of the page in FIG. 2.

The instant volumetric flow gauge is shown in its entirety in FIGS. 2 and 5. It consists of a tube 5, having an internal chamber 6 which, as shown in FIG. 5, is slightly inwardly tapered toward the bottom to produce a more accurate volumetric flow gauging. The top of the tube is covered with a cap 7 having a vent hole 8, and the bottom of the tube is formed into a body 9, which could be a separate piece or a piece integrally molded with the tube 5.

The body 9 has one fitting 10 which inserts into one of the tips 2 and communicates to the duct 11. The body defines a spaced plug 12, shaped similarly to the fitting 10, which inserts into the other tip 2 of the cannula 3, blocking this tip so that all the oxygen is forced up through the fitting 10 into the gauge 5.

Inside the chamber 6 is a ball 13, made of a weight which corresponds to the volumetric flow associated with the graduations 14 on the side of the transparent tube 5. Actually, the weight and size of the ball must of course be taken into account and correlated with the markings 14 so that an accurate measure of the volumetric flow of gas through the tube is obtainable.

At the bottom of the tube 6 the body 9 defines a shoulder 15 which prevents the ball from lodging between the converging walls of the tube. The vent cap at the top of course prevents exit of the ball from the top, and as the tube is not tapered upwardly, the ball 13 will not become wedged in the upper portion of the tube or the cap 7.

The instant invention, being simple in concept, economical to make, and soon to be universally available to all oxygen patients, is not only a convenience, but serves a substantial health need for oxygen-using outpatients. Virtually any out-patient utilizing oxygen supplied through an oxygen line could use this simple, yet effective volumetric flow gauge. Although for most it would simply mean remaining more alert and felling better, for some, it would make the difference, either immediately or over a period of time, between life or death.

What is claimed is:

1. A volumetric flow meter for detecting the oxygen flow from an oxygen delivery apparatus having at least one nasal cannula outlet comprising:
   (a) indicator means proportionately responsive to gas flow to indicate the volumetric flow of gas passing therethrough per unit of time;
   (b) nasal cannula fitting means connected to said indicator means and configured to be connected to said at least one nasal cannula outlet to receive the oxygen flowing therefrom and direct same to said indicator for measurement of the volumetric flow of said oxygen.

2. Structure according to claim 1 wherein said indicator means comprises a hollow tube with volumetric flow indicia thereon to be held upright and having a vented top, said fitting means directs oxygen to the bottom of said tube, and including a floating ball in said tube such that elevation of said ball in said tube indicates upward oxygen flow therethrough.

3. Structure according to claim 2 wherein said hollow tube has an inward taper from the top to the bottom to define a slightly conical gas chamber, and said tube is transparent and said indicia comprises graduation marks spaced along the side thereof to indicate the level of volumetric gas flow therein.

4. Structure according to claim 3 wherein said oxygen delivery apparatus could be of the type having two nasal cannula outlets and said fitting means is shaped and dimensioned to be inserted into one of said nasal cannula outlets and further includes means to seal the other nasal cannula outlet.

5. Structure according to claim 4 wherein said means to seal comprises a tapered plug spaced from said fitting means on the order of the distance between said two nasal cannula outlets.

6. Structure according to claim 5 wherein said tube, fitting means and plug are all molded as a single piece.

7. Structure according to claim 6 and including a removable vent cap mount on the top of said tube.

8. Structure according to claim 6 and including a shoulder at the lower end of said tube defining a bottom seat for said ball in said chamber to prevent said ball from becoming wedged in the tapered chamber.

9. A method of measuring the volumetric flow of oxygen from a two-tip nasal cannula with a hollow tube having volumetric flow indicia thereon and a floating ball therein comprising:
   (a) connecting the bottom of said tube, while upright, to one of the tips of said cannula;
   (b) sealing the other tip of said cannula;
   (c) gauging the level to which said ball rises in said tube in response to oxygen lifting same; and,
   (d) comparing said level to a calibrated standard.

10. A method according to claim 9 wherein a gauge is used having a fitting insertable into one of said tips and an integral plug spaced from said fitting to seal the other of said tips, and step (a) includes inserting said fitting in one tip and step (b) comprises seating said plug into the other of said tip.

* * * * *